United States Patent
Mickiewicz et al.

(10) Patent No.: US 12,349,943 B2
(45) Date of Patent: Jul. 8, 2025

(54) CONNECTORS FOR USE IN SYSTEMS AND METHODS FOR REDUCING THE RISK OF PROXIMAL JUNCTIONAL KYPHOSIS

(71) Applicant: Medos International Sarl, Le Locle (CH)

(72) Inventors: Christopher Mickiewicz, Bridgewater, MA (US); Michael O'Neil, West Barnstable, MA (US); Connor Engstrom, Hopkinton, MA (US); Michael O'Brien, Dallas, TX (US); Christopher Ames, Mill Valley, CA (US); Munish Gupta, Frontenac, MO (US); Matthew Scott-Young, Southport (AU)

(73) Assignee: Medos International Sàrl, Le Locle (CH)

( * ) Notice: Subject to any disclaimer, the term of this patent is extended or adjusted under 35 U.S.C. 154(b) by 446 days.

(21) Appl. No.: 17/687,161

(22) Filed: Mar. 4, 2022

(65) Prior Publication Data
US 2022/0183724 A1  Jun. 16, 2022

Related U.S. Application Data

(63) Continuation of application No. 16/584,597, filed on Sep. 26, 2019, now Pat. No. 11,298,158, which is a
(Continued)

(51) Int. Cl.
*A61B 17/70* (2006.01)

(52) U.S. Cl.
CPC ...... *A61B 17/7043* (2013.01); *A61B 17/7047* (2013.01); *A61B 17/7049* (2013.01); *A61B 17/7067* (2013.01); *A61B 2017/7073* (2013.01)

(58) Field of Classification Search
CPC ...... A61B 17/70; A61B 17/7019–7031; A61B 17/7049–7058; A61B 17/7062–707
See application file for complete search history.

(56) References Cited

U.S. PATENT DOCUMENTS

| | | | |
|---|---|---|---|
| 4,570,618 | A | 2/1986 | Wu |
| 5,030,220 | A | 7/1991 | Howland |

(Continued)

FOREIGN PATENT DOCUMENTS

| | | |
|---|---|---|
| CN | 1859880 A | 11/2006 |
| CN | 101568308 A | 10/2009 |

(Continued)

OTHER PUBLICATIONS

U.S. Appl. No. 15/663,856, filed Jul. 31, 2017, Systems and Methods for Reducing the Risk of Proximal Junctional Kyphosis Using a Bone Anchor or Other Attachment Point.
(Continued)

*Primary Examiner* — Eduardo C Robert
*Assistant Examiner* — Michelle C Green
(74) *Attorney, Agent, or Firm* — Barnes & Thornburg LLP (57) ABSTRACT

Systems and methods for reducing the risk of PJK, PJF, and other conditions are disclosed herein. In some embodiments, a longitudinal extension can be added to a primary fixation construct to extend the construct to one or more additional vertebral levels. The extension can be attached to a first attachment point, such as a spinous process of a vertebra that is superior to the primary construct. The extension can also be attached to a second attachment point, such as a component of the primary construct or an anatomical structure disposed inferior to the first attachment point. The extension can be more flexible than the primary construct and/or can limit motion to a lesser degree than the primary construct,
(Continued)

thereby providing a more-gradual transition from the instrumented vertebrae to the natural patient anatomy adjacent thereto. The extension can be placed with little or no soft tissue disruption.

11 Claims, 6 Drawing Sheets

Related U.S. Application Data continuation of application No. 15/663,865, filed on Jul. 31, 2017, now Pat. No. 10,456,174.

(56) References Cited

U.S. PATENT DOCUMENTS

| | | |
|---|---|---|
| 5,190,545 A | 3/1993 | Corsi et al. |
| 5,318,566 A | 6/1994 | Miller |
| 5,395,374 A | 3/1995 | Miller et al. |
| 5,415,658 A | 5/1995 | Kilpela et al. |
| 5,417,690 A | 5/1995 | Sennett et al. |
| 5,454,812 A | 10/1995 | Lin |
| 5,456,722 A | 10/1995 | McLeod et al. |
| 5,496,318 A | 3/1996 | Howland et al. |
| 5,540,698 A | 7/1996 | Preissman |
| 5,540,703 A | 7/1996 | Barker, Jr. et al. |
| 5,609,634 A | 3/1997 | Voydeville |
| 5,649,927 A | 7/1997 | Kilpela et al. |
| 5,702,399 A | 12/1997 | Kilpela et al. |
| 5,725,582 A | 3/1998 | Bevan et al. |
| 5,772,663 A | 6/1998 | Whiteside et al. |
| 5,782,831 A | 7/1998 | Sherman et al. |
| 5,899,903 A | 5/1999 | Cotrel |
| 6,086,590 A | 7/2000 | Margulies et al. |
| 6,099,527 A | 8/2000 | Hochschuler et al. |
| 6,277,120 B1 | 8/2001 | Lawson |
| 6,312,431 B1 | 11/2001 | Asfora |
| 6,391,030 B1 | 5/2002 | Wagner et al. |
| 6,436,099 B1 | 8/2002 | Drewry et al. |
| 6,514,255 B1 | 2/2003 | Ferree |
| 6,582,434 B2 | 6/2003 | Kawakami et al. |
| 6,605,091 B1 | 8/2003 | Iwanski |
| 6,946,000 B2 | 9/2005 | Senegas et al. |
| 7,087,083 B2 | 8/2006 | Pasquet et al. |
| 7,250,054 B2 | 7/2007 | Allen et al. |
| 7,666,208 B1 | 2/2010 | Asfora |
| 7,682,376 B2 | 3/2010 | Trieu |
| 7,717,938 B2 | 5/2010 | Kim et al. |
| 7,717,939 B2 | 5/2010 | Ludwig et al. |
| 8,177,810 B2 | 5/2012 | Ferree |
| 8,246,655 B2 | 8/2012 | Jackson et al. |
| 8,308,771 B2 | 11/2012 | Bennett et al. |
| 8,313,513 B2 | 11/2012 | Beger et al. |
| 8,333,791 B2 | 12/2012 | Carls et al. |
| 8,361,117 B2 | 1/2013 | Michielli et al. |
| 8,394,128 B2 | 3/2013 | Kothari et al. |
| 8,403,964 B2 | 3/2013 | Fielding et al. |
| 8,419,772 B2 | 4/2013 | Thompson et al. |
| 8,465,527 B2 | 6/2013 | Clement |
| 8,529,607 B2 | 9/2013 | Alamin et al. |
| 8,696,710 B2 | 4/2014 | Fielding et al. |
| 8,740,941 B2 | 6/2014 | Thramann |
| 8,758,409 B2 | 6/2014 | Hochschuler et al. |
| 8,758,411 B1 | 6/2014 | Rayon et al. |
| 8,845,689 B2 | 9/2014 | Douget et al. |
| 8,870,881 B2 | 10/2014 | Rezach et al. |
| 8,926,668 B2 | 1/2015 | Douget |
| 8,940,019 B2 | 1/2015 | Gordon et al. |
| 8,979,897 B2 | 3/2015 | Butterfield et al. |
| 8,979,899 B2 | 3/2015 | Ciupik et al. |
| 9,084,637 B2 | 7/2015 | Pasquet et al. |
| 9,144,440 B2 | 9/2015 | Aminian |
| 9,186,185 B2 | 11/2015 | Hestad et al. |
| 9,265,532 B2 | 2/2016 | Lamborne et al. |
| 9,295,496 B2 | 3/2016 | Le Couedic et al. |
| 9,295,499 B2 | 3/2016 | Alamin et al. |
| 9,314,275 B2 | 4/2016 | Clement et al. |
| 9,421,044 B2 | 8/2016 | Blain et al. |
| 9,439,686 B2 | 9/2016 | Rooney et al. |
| 9,585,705 B2 | 3/2017 | Koch et al. |
| 9,642,653 B2 | 5/2017 | Scarrow et al. |
| 9,668,773 B2 | 6/2017 | Alexander et al. |
| 9,675,386 B2 | 6/2017 | Akbarnia et al. |
| 9,770,268 B2 | 9/2017 | Albert et al. |
| 9,848,919 B2 | 12/2017 | Simpson et al. |
| 9,861,391 B2 | 1/2018 | Larroque-Lahitette |
| 9,901,377 B2 | 2/2018 | Legallois |
| 9,924,970 B2 | 3/2018 | Gordon |
| 9,924,976 B2 | 3/2018 | Simpson et al. |
| 9,949,778 B2 | 4/2018 | Baccelli et al. |
| 9,993,274 B2 | 6/2018 | Belliard |
| 10,034,692 B2 | 7/2018 | Palmer et al. |
| 10,098,673 B2 | 10/2018 | Rooney et al. |
| 10,456,174 B2 | 10/2019 | Mickiewicz et al. |
| 10,463,403 B2 | 11/2019 | Mickiewicz et al. |
| 10,512,486 B2 | 12/2019 | Larroque-Lahitette |
| 11,207,107 B2 | 12/2021 | Mickiewicz et al. |
| 11,284,924 B1 | 3/2022 | Italiaie et al. |
| 11,298,158 B2 | 4/2022 | Mickiewicz et al. |
| 2003/0187435 A1* | 10/2003 | Lin ............... A61B 17/7001 606/252 |
| 2004/0248078 A1 | 12/2004 | Manolagas et al. |
| 2005/0010227 A1* | 1/2005 | Paul ............... A61B 17/8023 606/71 |
| 2005/0080420 A1 | 4/2005 | Farris et al. |
| 2005/0192581 A1 | 9/2005 | Molz et al. |
| 2005/0245929 A1 | 11/2005 | Winslow et al. |
| 2006/0241601 A1* | 10/2006 | Trautwein .......... A61B 17/7067 606/279 |
| 2006/0247625 A1 | 11/2006 | Morrison et al. |
| 2007/0043365 A1 | 2/2007 | Ritland |
| 2007/0073293 A1 | 3/2007 | Martz et al. |
| 2007/0093823 A1 | 4/2007 | Booth et al. |
| 2007/0233089 A1 | 10/2007 | DiPoto et al. |
| 2007/0299445 A1 | 12/2007 | Shadduck et al. |
| 2008/0009866 A1 | 1/2008 | Alamin et al. |
| 2008/0140133 A1 | 6/2008 | Allard et al. |
| 2008/0177326 A1 | 7/2008 | Thompson |
| 2008/0234744 A1 | 9/2008 | Zylber et al. |
| 2008/0294199 A1 | 11/2008 | Kohm et al. |
| 2009/0149885 A1* | 6/2009 | Durward ............ A61B 17/7067 606/279 |
| 2009/0177233 A1 | 7/2009 | Malek |
| 2009/0204151 A1 | 8/2009 | Bracken |
| 2009/0248081 A1 | 10/2009 | Lehuec et al. |
| 2009/0270918 A1 | 10/2009 | Attia et al. |
| 2010/0069961 A1 | 3/2010 | DiPoto et al. |
| 2010/0137913 A1 | 6/2010 | Khatchadourian et al. |
| 2010/0292736 A1 | 11/2010 | Schwab |
| 2010/0318133 A1* | 12/2010 | Tornier ............. A61B 17/7067 606/270 |
| 2011/0004248 A1 | 1/2011 | Abdou |
| 2011/0009906 A1 | 1/2011 | Hestad et al. |
| 2011/0137345 A1 | 6/2011 | Stoll et al. |
| 2011/0172708 A1 | 7/2011 | Fielding et al. |
| 2011/0172709 A1 | 7/2011 | Lyons et al. |
| 2011/0245875 A1 | 10/2011 | Karim |
| 2011/0270314 A1 | 11/2011 | Mueller et al. |
| 2011/0288589 A1 | 11/2011 | Fielding et al. |
| 2012/0041441 A1 | 2/2012 | Bernstein et al. |
| 2012/0078303 A1 | 3/2012 | Malek |
| 2012/0109200 A1 | 5/2012 | Cahill et al. |
| 2012/0109202 A1 | 5/2012 | Kretzer et al. |
| 2012/0109210 A1 | 5/2012 | Baker et al. |
| 2012/0136390 A1* | 5/2012 | Butler ............... A61B 17/7067 606/248 |
| 2012/0150231 A1 | 6/2012 | Alamin et al. |
| 2013/0012955 A1 | 1/2013 | Lin |
| 2013/0035727 A1 | 2/2013 | Datta |
| 2013/0072983 A1 | 3/2013 | Lindquist et al. |
| 2013/0090692 A1 | 4/2013 | Nuckley et al. |
| 2013/0123854 A1 | 5/2013 | Kondrashov et al. |
| 2013/0150887 A1 | 6/2013 | McLean et al. |

(56) References Cited

U.S. PATENT DOCUMENTS

| | | | |
|---|---|---|---|
| 2013/0238033 A1* | 9/2013 | Black | A61B 17/70 606/286 |
| 2013/0274808 A1 | 10/2013 | Larroque-Lahitette et al. | |
| 2013/0325065 A1 | 12/2013 | Malandain et al. | |
| 2013/0325068 A1 | 12/2013 | Fielding et al. | |
| 2013/0345753 A1 | 12/2013 | Kretzer et al. | |
| 2014/0025116 A1 | 1/2014 | Wei | |
| 2014/0052183 A1 | 2/2014 | Freese | |
| 2014/0074166 A1* | 3/2014 | Scarrow | A61B 17/7067 606/247 |
| 2014/0094851 A1 | 4/2014 | Gordon | |
| 2014/0135839 A1 | 5/2014 | Frankel et al. | |
| 2014/0155940 A1 | 6/2014 | Dubois et al. | |
| 2014/0222076 A1 | 8/2014 | Jackson | |
| 2014/0257396 A1 | 9/2014 | Powers et al. | |
| 2014/0277142 A1 | 9/2014 | Blain et al. | |
| 2014/0277145 A1 | 9/2014 | Reitblat et al. | |
| 2014/0277163 A1 | 9/2014 | Kretzer et al. | |
| 2014/0296917 A1 | 10/2014 | Donner et al. | |
| 2015/0182263 A1* | 7/2015 | Donner | A61B 17/7067 606/248 |
| 2015/0190178 A1 | 7/2015 | McCarthy et al. | |
| 2016/0106478 A1 | 4/2016 | Simpson et al. | |
| 2016/0143670 A1 | 5/2016 | Alamin et al. | |
| 2016/0166289 A1 | 6/2016 | Alsup et al. | |
| 2016/0235447 A1 | 8/2016 | Mundis, Jr et al. | |
| 2016/0242819 A1 | 8/2016 | Simpson et al. | |
| 2016/0249957 A1 | 9/2016 | Deneuvillers | |
| 2016/0287299 A1 | 10/2016 | Lang | |
| 2016/0310170 A1 | 10/2016 | Carls | |
| 2016/0354118 A1 | 12/2016 | Belliard et al. | |
| 2017/0007299 A1* | 1/2017 | Mundis, Jr. | A61B 17/7049 |
| 2017/0086889 A1 | 3/2017 | Padilla et al. | |
| 2017/0231661 A1 | 8/2017 | Bannigan et al. | |
| 2017/0281232 A1 | 10/2017 | Smith et al. | |
| 2017/0281237 A1 | 10/2017 | Murray et al. | |
| 2017/0281246 A1 | 10/2017 | Murray et al. | |
| 2017/0281247 A1 | 10/2017 | Murray et al. | |
| 2017/0325850 A1 | 11/2017 | Acosta | |
| 2017/0333087 A1 | 11/2017 | Lee et al. | |
| 2017/0333088 A1 | 11/2017 | Lee et al. | |
| 2017/0348024 A1 | 12/2017 | Abell et al. | |
| 2017/0348026 A1 | 12/2017 | Stein et al. | |
| 2018/0078286 A1 | 3/2018 | Le Couëdic et al. | |
| 2018/0098798 A1 | 4/2018 | Italiaie et al. | |
| 2018/0110544 A1 | 4/2018 | Simpson et al. | |
| 2018/0116695 A1 | 5/2018 | Armstrong et al. | |
| 2018/0161069 A1 | 6/2018 | DiPaola | |
| 2018/0168694 A1 | 6/2018 | Lee et al. | |
| 2018/0228516 A1 | 8/2018 | Armstrong et al. | |
| 2018/0228518 A1 | 8/2018 | Carruth et al. | |
| 2018/0243009 A1 | 8/2018 | Bobbitt et al. | |
| 2018/0243012 A1 | 8/2018 | Bobbitt et al. | |
| 2018/0280062 A1 | 10/2018 | Lee et al. | |
| 2018/0280063 A1 | 10/2018 | Lee et al. | |
| 2018/0289403 A1 | 10/2018 | Shoshtaev | |
| 2018/0353216 A1 | 12/2018 | Mundis, Jr et al. | |
| 2019/0029733 A1 | 1/2019 | Mickiewicz et al. | |
| 2019/0029734 A1 | 1/2019 | Mickiewicz et al. | |
| 2020/0015860 A1 | 1/2020 | Mickiewicz et al. | |
| 2020/0015862 A1 | 1/2020 | Mickiewicz et al. | |
| 2022/0202453 A1 | 6/2022 | Mickiewicz et al. | |

FOREIGN PATENT DOCUMENTS

| | | |
|---|---|---|
| CN | 102046107 A | 5/2011 |
| CN | 102869309 A | 1/2013 |
| CN | 101677828 8 | 5/2013 |
| CN | 204233205 U | 4/2015 |
| CN | 104902855 A | 9/2015 |
| CN | 104768484 B | 10/2017 |
| EP | 0928603 A1 | 7/1999 |
| EP | 1205152 B1 | 9/2004 |
| JP | 2001314416 A | 11/2001 |
| JP | 2008535583 A | 9/2008 |
| JP | 2013525006 A | 6/2013 |
| JP | 2014534862 A | 12/2014 |
| TW | 200738210 A | 10/2007 |
| WO | 1999044526 A1 | 9/1999 |
| WO | 2007052975 A1 | 5/2007 |
| WO | 2008051802 A2 | 5/2008 |
| WO | 2009099477 A2 | 8/2009 |
| WO | 2012122408 A1 | 9/2012 |

OTHER PUBLICATIONS

U.S. Appl. No. 15/663,865, filed Jul. 31, 2017, Connectors for Use in Systems and Methods for Reducing the Risk for Proximal Junctional Kyphosis.
U.S. Appl. No. 16/584,528, filed Sep. 26, 2019, Systems and Methods for Reducing the Risk of Proximal Junctional Kyphosis Using a Bone Anchor or Other Attachment Point.
U.S. Appl. No. 16/584,597, filed Sep. 26, 2019, Connectors for Use in Systems and Methods for Reducing the Risk of Proximal Junctional Kyphosis.
U.S. Appl. No. 17/539,994, filed Dec. 1, 2021, Systems and Methods for Reducing the Risk of Proximal Junctional Kyphosis Using a Bone Anchor or Other Attachment Point.
Japanese Office Action for Application No. 2020-505255, dated Jan. 10, 2023.
Chinese Office Action for Application No. 201880055719.1, dated Nov. 9, 2022 (19 pages).
Office Action for Application No. 2020-505255, dated Jan. 10, 2023.
[NoAuthorListed] YouTube™ webpage; "NILE™ Alternative Fixation Spinal System Product Animation," K2MInc, Mar. 25, 2015; retrieved online Dec. 7, 2017; <https://www.youtube.com/watch?v=7R76zxh5NkM >.
Extended European Search Report for Application No. 18841050.0, dated Mar. 30, 2021 (11 pages).
Extended European Search Report for Application No. 18842199.4, dated Apr. 6, 2021 (11 pages).
International Search Report and Written Opinion for Application No. PCT/US2018/044623, mailed Dec. 10, 2018 (12 pages).
International Search Report and Written Opinion for Application No. PCT/US2018/044631, mailed Dec. 12, 2018 (15 pages).
Japanese Office Action for Application No. 2020-505211, dated May 17, 2022 (11 pages).
Japanese Office Action for Application No. 2020-505255, dated May 24, 2022 (10 pages).

* cited by examiner

CONNECTORS FOR USE IN SYSTEMS AND METHODS FOR REDUCING THE RISK OF PROXIMAL JUNCTIONAL KYPHOSIS

CROSS REFERENCE TO RELATED APPLICATIONS

This application is a continuation of U.S. application Ser. No. 16/584,597, filed on Sep. 26, 2019, entitled "Connectors for Use in Systems and Methods for Reducing the Risk of Proximal Junctional Kyphosis." U.S. application Ser. No. 16/584,597, is a continuation of U.S. application Ser. No. 15/663,865, filed Jul. 31, 2017, entitled "Connectors for Use in Systems and Methods for Reducing the Risk of Proximal Junctional Kyphosis," and now issued as U.S. Pat. No. 10,456,174. The entire contents of each of these applications are hereby incorporated by reference.

FIELD

Systems and methods for reducing the risk of proximal junctional kyphosis (PJK), proximal junctional failure (PJF), and other conditions are disclosed herein.

BACKGROUND

There are a number of spinal surgeries in which a fixation or stabilization construct is implanted in a patient and attached to the patient's spine. For example, a typical posterior fixation construct may include one or more longitudinal spinal rods attached to multiple of the patient's vertebrae by respective bone anchors. Exemplary bone anchors can include pedicle or lateral mass screws, hooks, wires, and so forth. The implanted construct extends along a segment of the spine between an uppermost instrumented vertebra (UIV), i.e., the most-superior or most-cranial vertebra to which the construct is attached, and a lowermost instrumented vertebra (LIV), i.e., the most-inferior or most-caudal vertebra to which the construct is attached.

Figures 1, 2A, 2B:
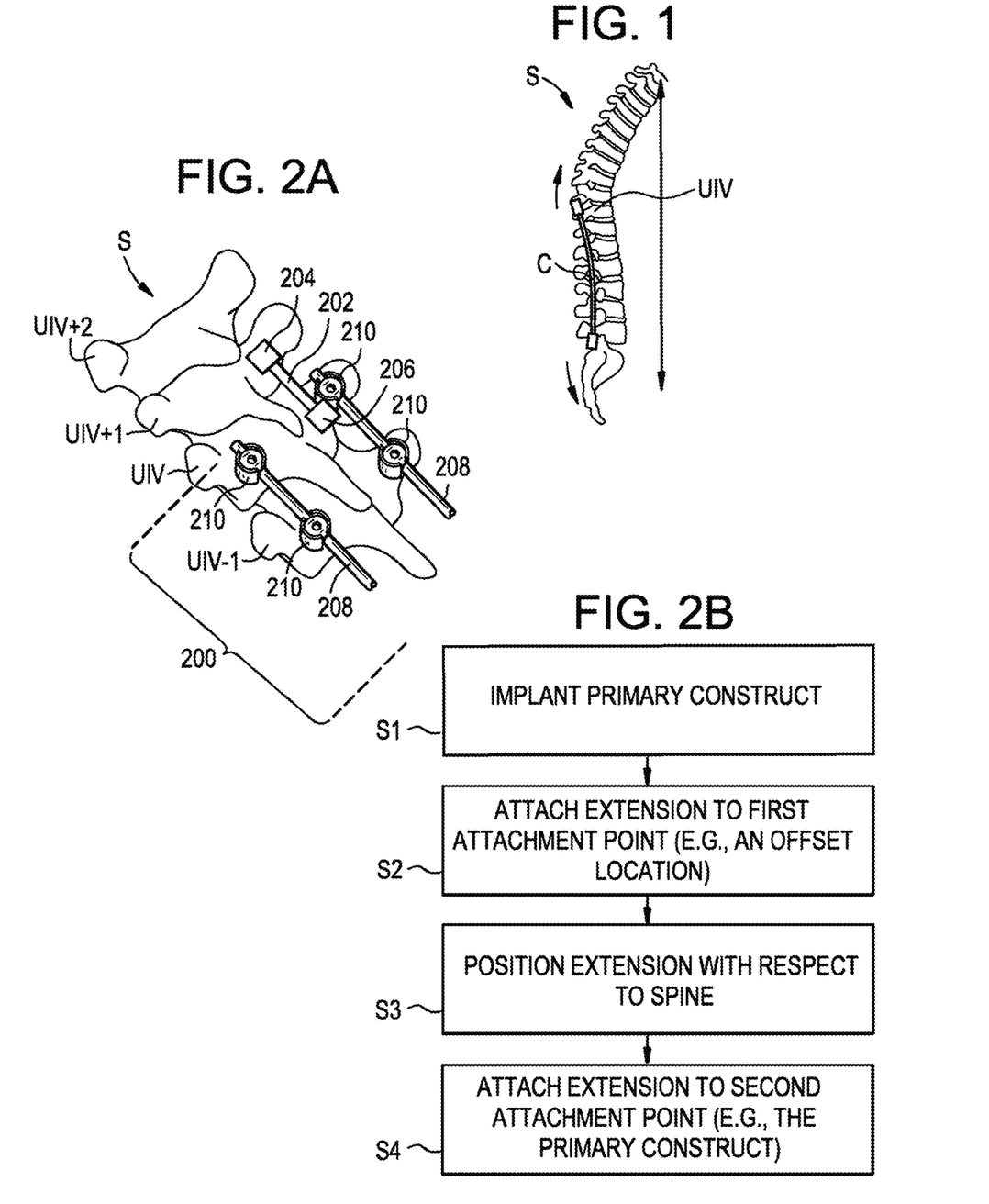
FIG. 1 is a sagittal view of the spine of a human patient suffering from PJK/PJF.
FIG. 2A is a perspective view of a human spine with a primary construct and a longitudinal extension attached thereto.
FIG. 2B is a flow chart of a surgical method.

One complication that can arise with these surgeries is an undesired degree of kyphosis at or above the UIV. Proximal junctional kyphosis (PJK) is typically defined as a proximal junctional sagittal Cobb angle greater than 10 degrees, or at least 10 degrees greater than in a pre-operative measurement. It is estimated that between 5% and 46% of adult spine patients suffer from some form of PJK, with most cases being diagnosed weeks or months after the surgery. In some cases, proximal junctional failure (PJF) can occur. PJF may be characterized by (i) post-operative fracture of the UIV or the vertebra superiorly-adjacent thereto (UIV+1), (ii) UIV implant failure, (iii) PJK increase greater than 15 degrees, and/or (iv) a need for proximal extension of the fusion or the construct within 6 months of the surgery. FIG. 1 is a sagittal view of a patient spine S in which PJK/PJF has occurred above the UIV after surgery to implant a fixation construct C. Patients who suffer from PJK or PJF may experience increased pain, neurologic deficit, or ambulatory difficulties, and may be faced with revision surgery and the expenses and risks associated therewith.

SUMMARY

Systems and methods for reducing the risk of PJK, PJF, and other conditions are disclosed herein. In some embodiments, a longitudinal extension can be added to a primary fixation construct to extend the construct to one or more additional vertebral levels. The extension can be attached to a first attachment point, such as a spinous process of a vertebra that is superior to the primary construct. The extension can also be attached to a second attachment point, such as a component of the primary construct or an anatomical structure disposed inferior to the first attachment point. The extension can be more flexible than the primary construct and/or can limit motion to a lesser degree than the primary construct, thereby providing a more-gradual transition from the instrumented vertebrae to the natural patient anatomy adjacent thereto. The extension can be placed with little or no soft tissue disruption.

In some embodiments, a surgical method can include attaching a primary construct to a spine of a patient, the primary construct extending between an uppermost instrumented vertebra (UIV) and a lowermost instrumented vertebra (LIV); attaching a connector to a first attachment point, the first attachment point comprising a spinous process disposed superior to the UIV of the primary construct; positioning the connector relative to the patient's spine; and attaching the connector to a second attachment point, the second attachment point being disposed at or inferior to the UIV of the primary construct.

The first attachment point can include a plurality of spinous processes disposed superior to the UIV of the primary construct. The second attachment point can include first and second spinal rods of the primary construct. The second attachment point can include first and second bone anchors of the primary construct. The connector can include a main body with first and second arms extending in a superior direction therefrom. Attaching the connector to the second attachment point can include attaching opposed connection points of the main body to contralateral components of the primary construct. The arms can be curved in the sagittal plane and can apply extension forces to the patient's spine. Attaching the connector to the first attachment point can include urging teeth formed on the arms into engagement with the spinous process. Attaching the connector to the first attachment point can include positioning first portions of each arm in contact with respective lateral surfaces of the spinous process and positioning second portions of each arm in contact with a superior surface of the spinous process. Attaching the connector to the first attachment point can include suturing or riveting the arms of the connector to the spinous process. Attaching the connector to the first attachment point can include applying sutures through apertures formed in the arms. Positioning the connector relative to the patient's spine can include at least one of: (i) longitudinally translating the arms relative to the main body within recesses formed in the main body and (ii) tilting the arms relative to the main body within recesses formed in the main body. Positioning the connector relative to the patient's spine can include tightening a locking mechanism of the connector to lock a position and/or orientation of the arms relative to the main body. Positioning the connector can include spreading the arms of the connector apart from one another to allow the spinous process to be inserted therebetween and then returning the arms towards one another to capture the spinous process within a space defined between the arms.

Attaching the connector to the first attachment point can include rotating or sliding a collar with respect to the arms of the connector to clamp the arms onto the spinous process. The arms can have a stiffness that is greater than a stiffness of patient anatomy superior to the UIV of the primary construct and that is less than a stiffness of the primary construct. The arms can have a degree of spinal motion restriction that is greater than that of patient anatomy superior to the UIV of the primary construct and less than that of the primary construct. The arms can limit flexion of the spine without completely preventing such flexion. The primary construct can be implanted through a primary incision and the connector can be positioned relative to the patient's spine and attached to the first and second attachment points through the primary incision. The primary incision can have a superior terminal end that is disposed at or inferior to the UIV of the primary construct. Positioning the connector relative to the patient's spine can include tunneling first and second arms of the connector in a superior direction from the primary incision to position the arms alongside a plurality of spinous processes disposed superior to a superior terminal end of the primary incision. Attaching the connector to the second attachment point can include threading an elongate flexible tether through one or more apertures of the connector and attaching the tether to the primary construct. In some embodiments, vertebrae instrumented with the primary construct are fused to one another or prepared for such fusion and vertebrae to which the primary construct is extended by the connector are not fused or prepared for fusion. The primary construct can include a rigid spinal rod attached to first and second vertebrae by respective bone anchors. In some embodiments, no portion of the connector is disposed anterior to any lamina of the patient's spine when the connector is attached to the first and second attachment points.

In some embodiments, a surgical system can include a primary construct comprising a rigid spinal fixation rod and first and second bone anchors configured to attach the spinal rod to first and second vertebrae; and a connector comprising: a main body having at least one attachment point for attaching the connector to the primary construct; and first and second arms extending in a superior direction from the main body.

The at least one attachment point can include first and second rod receiving recesses disposed at opposite ends of the main body. The main body can include a transverse strut extending between the first and second rod receiving recesses. The first and second arms can extend superiorly from the transverse strut. The arms can include bone engaging teeth or surface features formed thereon. The arms can be shaped to wrap around the superior edge of a spinous process. The arms can be shaped to simultaneously contact a lateral surface of a spinous process and a superior surface of said spinous process. The arms can be selectively translatable and/or rotatable relative to the main body. The main body can include a locking mechanism configured to lock a position and/or orientation of the arms relative to the main body. The arms can be more flexible than the spinal rod. The arms can extend superiorly from the main body by a length of at least two vertebral levels of an adult human patient. The arms can include apertures for receiving a fastener therethrough. The arms can merge into a single arm as they approach the main body. The system can include a collar that is rotatable and/or slidable relative to the arms to move the arms towards one another. The collar can include an interior thread engaged with an exterior thread of the arms, at least one of the interior and exterior threads being tapered. The system can include an elongate flexible tether insertable through one or more openings formed in the main body of the connector. The main body can include one or more locking elements configured to clamp onto the tether when the tether is disposed through the one or more openings.

DETAILED DESCRIPTION

Systems and methods for reducing the risk of PJK, PJF, and other conditions are disclosed herein. In some embodiments, a longitudinal extension can be added to a primary fixation construct to extend the construct to one or more additional vertebral levels. The extension can be attached to a first attachment point, such as a spinous process of a vertebra that is superior to the primary construct. The extension can also be attached to a second attachment point, such as a component of the primary construct or an anatomical structure disposed inferior to the first attachment point. The extension can be more flexible than the primary construct and/or can limit motion to a lesser degree than the primary construct, thereby providing a more-gradual transition from the instrumented vertebrae to the natural patient anatomy adjacent thereto. The extension can be placed with little or no soft tissue disruption.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments. The features illustrated or described in connection with one exemplary embodiment may be combined with the features of other embodiments.

FIGS. 2A-2B schematically illustrate a system and method for treating, preventing, or reducing the risk of proximal junctional kyphosis, proximal junctional failure, and other conditions. As shown, a primary construct 200 can be implanted in a patient and attached to the patient's spine S. The primary construct 200 can be extended to one or more additional vertebral levels by (i) attaching a longitudinal extension 202 to a first attachment point 204, (ii) positioning the longitudinal extension relative to the patient's spine, and (iii) attaching the longitudinal extension to a second attachment point 206. The first attachment point 204 can be an implant or an anatomical structure that is longitudinally offset from the primary construct 200, e.g., one or more vertebral levels superior to the UIV of the primary construct. The extension 202 can be attached to the first attachment point 204 in a manner that does not disrupt or only minimally disrupts soft tissue in the vicinity of the first attachment point. The second attachment point 206 can be an implant or an anatomical structure disposed at or below the UIV of the primary construct 200. For example, the second attachment point can be a rod 208, bone anchor 210, or other component of the primary construct 200 itself, or a vertebra to which the primary construct is attached. The above steps can be performed in any sequence. For example, the extension 202 can be implanted prior to the primary construct 200. As another example, the extension 202 can be attached to the first attachment point 204 after placing the extension in its final position relative to the spine and/or after attaching the extension to the second attachment point 206.

The extension can provide a step-down in stiffness and/or spinal motion restriction between the primary construct (which is typically relatively rigid and immobile) and the natural soft tissue and other patient anatomy superior to the primary construct (to which there is generally no implant-based rigidity or mobility restriction applied). The extension can have a stiffness that is greater than the natural patient anatomy and less than the primary construct. The extension can have a degree of spinal motion restriction that is greater than the natural patient anatomy and less than the primary construct. The extension can help insulate the patient anatomy superior to the primary construct from forces and stress that may contribute to PJK/PJF. The extension can provide a soft link between the primary construct and undisturbed soft tissue superior thereto. The extension can constrain or limit flexion of the spine to reduce the risk of PJK/PJF. The extension can replicate the natural soft tissue envelope. In some embodiments, the vertebrae instrumented with the primary construct are fused to one another and the vertebrae to which the primary construct is extended by the extension are not fused. Accordingly, a hybrid construct can be formed in which a first spinal segment is instrumented and fused, a second spinal segment superior to the first segment is instrumented and not fused, and a third spinal segment superior to the second segment is neither instrumented nor fused.

Referring now to FIG. 2B, in a step S1, a primary construct can be implanted in the patient. The primary construct can include one or more spinal rods extending longitudinally along the patient's spine. The spinal rod or rods can be attached to the patient's spine using bone anchors such as pedicle or lateral mass screws, hooks, wires, and so forth. The primary construct can extend along a segment of the spine between an uppermost instrumented vertebra (UIV) of the primary construct, i.e., the most-superior or most-cranial vertebra to which the primary construct is attached, and a lowermost instrumented vertebra (LIV) of the primary construct, i.e., the most-inferior or most-caudal vertebra to which the primary construct is attached. The UIV can be the uppermost vertebra in which a bone screw of the primary construct is implanted. The LIV can be the lowermost vertebra in which a bone screw of the primary construct is implanted. The primary construct can be implanted using any of a variety of known techniques, including open procedures, minimally-invasive or percutaneous procedures, and so forth. The primary construct can be implanted through a primary incision. The primary incision can extend longitudinally along the patient's spine. The terminal superior end of the primary incision can be located inferior to UIV+1, inferior to UIV, and/or inferior to UIV−1. The primary incision can include a plurality of discrete incisions, e.g., in the case of minimally-invasive procedures for installing the primary construct. The primary construct can include a rigid spinal rod, e.g., a rod that does not materially bend or deform post-implantation when subjected to normal anatomical loads, or a rod which is not designed to bend or deform under such conditions.

In a step S2, a longitudinal extension can be attached to a first attachment point, e.g., a location within the patient that is offset from the primary construct. The extension can be or can include any of a variety of elements for extending the primary construct to one or more additional vertebral levels. For example, the extension can be a tether, cable, cord, mesh, fabric, tape, film, or wire. The extension can be flexible. The extension can have a stiffness that is less than that of the primary construct or a component thereof, e.g., less than a stiffness of a spinal rod of the primary construct. The extension can have a stiffness that is greater than that of the natural spinal anatomy, e.g., greater than that of the ligaments and other soft tissue that connect the vertebrae.

The extension can be connector of the type described below. The extension can be a length of MERSILENE tape available from ETHICON of Somerville, New Jersey. The extension can be a length of non-absorbable, braided, sterile material. The extension can be formed from poly (ethylene terephthalate). The extension can be formed from fibers of high molecular weight, long-chain, linear polyesters having recurrent aromatic rings. The extension can be coated with anti-bacterial agents, corticosteroids, anti-infective agents, tryclosan, and so forth. The extension can be radiopaque, radiolucent, or partially radiopaque and partially radiolucent. The extension can include imaging bands or markers. The extension can be polymeric. The extension can be formed from or can include various materials including polyethylene terephthalate or DACRON, polytetrafluoroethylene or TEFLON, polyparaphenylene terephthalamide or KEVLAR, ultra-high-molecular-weight polyethylene (UHMWPE), nylon, poly(L-lactic acid), and the like. The extension can be reinforced with materials including metals, elastomers, carbon fibers, etc. The extension can include resilient or shape memory materials such as elastomers or nitinol. Such materials can allow the extension to not only limit flexion of the spine, but also to instill extension forces, which may improve lordosis and/or reinforce posterior soft tissues. The extension forces can be tailored based upon material properties, weaving structure, thickness, or other attributes of the extension.

The extension can be a tether that is substantially flat or planar. The tether can have a cross-sectional width that is greater than a cross-sectional height. For example, the width can be at least two times greater than the height. The width of the tether can be in the range of about 4 mm to about 8 mm. The height of the tether can be in the range of about 0.5 mm to about 2.5 mm. The tether can have any number of different cross-sections, including rectangular, square, elliptical, circular, and so forth.

The extension can be attached to a first attachment point that is offset from the primary construct, e.g., one or more vertebral levels superior to the primary construct. The first attachment point can be a vertebra. The first attachment point can be a pedicle, a transverse process, a lamina, a facet, a spinous process, or a vertebral body of the vertebra. The first attachment point can be an implant implanted in any of the above locations. The vertebra can be superior to UIV. The vertebra can be UIV+1, UIV+2, or higher. The first attachment point can be a rib or other anatomical anchor point. The first attachment point can be a bone structure. The first attachment point can be a soft tissue structure. The first attachment point can be a muscle, a tendon, or a ligament. The extension can be attached to a plurality of the above-described first attachment points.

The extension can be attached to the first attachment point in any of a variety of ways. The extension can be attached to the first attachment point using a suture, rivet, or staple. The extension can be attached to the first attachment point using a clamp. The clamp can be attached to a lamina, spinous process, or other anatomical structure or implant. The extension can be attached to the first attachment point using a hook. The hook can be hooked onto a lamina, spinous process, or other anatomical structure or implant. The extension can be attached to the first attachment point using a bone anchor, e.g., a screw anchor, a suture anchor, an expandable anchor, a tether anchor, and/or a soft-tissue anchor, any of which may be of the type available from DEPUY SYNTHES of Raynham, Massachusetts.

The extension can be attached to the first attachment point in a way that minimizes soft tissue disruption. The extension can be positioned at the first attachment point without extending the primary incision and/or without forming any incision other than the primary incision. The extension can be positioned at the first attachment point through a small secondary incision formed over the first attachment point. The secondary incision can be percutaneous stab incision. The secondary incision can be made only as large as necessary to pass the extension therethrough, or only as large as necessary to pass an anchor for attaching the extension therethrough. The secondary incision can have a length that is equal or substantially equal (e.g., within 10% of) a corresponding dimension of the extension. The secondary incision can have a diameter that is equal or substantially equal (e.g., within 10% of) a diameter of a bone anchor used to attach the extension to the first attachment point. The secondary incision can have a length or diameter that is less than about 10 mm, less than about 5 mm, less than about 3 mm, and/or less than about 1 mm. The extension, or at least one end thereof, the anchor, or both the extension and the anchor, can be delivered to the first attachment point through a trocar, tube, or cannula. The extension can be attached to the first attachment point without disturbing the soft tissue envelope of the vertebral levels superior to the primary construct.

In a step S3, the extension can be positioned relative to the patient's spine. The extension can be positioned to extend along the patient's spine between the first attachment point and a second attachment point, such as the primary construct.

The extension can be passed through the secondary incision and then pushed and/or pulled in an inferior direction towards the primary construct, passing the extension beneath the skin and/or soft tissue disposed intermediate to the secondary incision and the primary construct. The extension can be pushed and/or pulled in the inferior direction by an inserter or tunneling instrument. The inserter instrument can be passed through the primary incision and up towards the secondary incision to grab the extension before pulling it inferiorly. The inserter instrument can be passed through the secondary incision and pushed with the extension coupled thereto inferiorly towards the primary construct, beneath the skin and/or soft-tissue.

The extension can be inserted through the primary incision and passed in a superior direction towards the first attachment point, guiding the extension beneath the skin and/or soft tissue disposed intermediate to the first attachment point and the primary incision. The extension can be passed in the superior direction using forceps, a pushrod, or other inserter instrument.

The extension can be positioned along a posterior aspect of the spine. The extension can be positioned along an anterior or lateral aspect of the spine. The extension can be positioned such that no portion of the extension is disposed anterior to any lamina of the patient's spine.

The extension can be positioned in a way that minimizes soft tissue disruption. The extension can be positioned without extending the primary incision and/or without forming any incision other than the primary incision. The extension can be positioned without disturbing the soft tissue envelope of the vertebral levels superior to the primary construct.

In a step S4, the extension can be attached to a second attachment point. The second attachment point can be inferior to the first attachment point. The second attachment point can be a spinal rod, a bone anchor or bone screw, a cross-connector, or any other component of the primary construct. The second attachment point can be an anatomical structure adjacent or inferior to the primary construct.

The second attachment point can be a vertebra. The second attachment point can be a pedicle, a transverse process, a lamina, a facet, a spinous process, or a vertebral body of the vertebra. The second attachment point can be an implant implanted in any of the above locations. The vertebra can be inferior to the UIV of the primary construct. The vertebra can be UIV, UIV−1, UIV−2, or lower. The second attachment point can be a rib or other anatomical anchor point. The second attachment point can be a bone structure. The second attachment point can be a soft tissue structure. The second attachment point can be a muscle, a tendon, or a ligament. The extension can be attached to a plurality of the above-described second attachment points.

The extension can be attached to the second attachment point in any of a variety of ways. The extension can be attached to the second attachment point using a suture, rivet, or staple. The extension can be attached to the second attachment point using a clamp. The clamp can be attached to a lamina, spinous process, or other anatomical structure or implant. The extension can be attached to the second attachment point using a hook. The hook can be hooked onto a lamina, spinous process, or other anatomical structure or implant. The extension can be attached to the second attachment point using a bone anchor, e.g., a screw anchor, a suture anchor, an expandable anchor, a tether anchor, and/or a soft-tissue anchor, any of which may be of the type available from DEPUY SYNTHES of Raynham, Massachusetts.

The second attachment point can be a spinal rod. The extension can be attached to the spinal rod using a clamp or connector that receives the rod and the extension.

The second attachment point can be a bone anchor, e.g., a screw or a hook. The extension can be attached to the bone anchor using a clamp or connector that receives the bone anchor and the extension. The extension can be clamped between a spinal rod and a rod seat of the bone anchor. The extension can be clamped between a spinal rod and a set screw or closure mechanism of the bone anchor. The bone anchor can include a first set screw or closure mechanism for locking the extension to the bone anchor and a second set screw or closure mechanism for locking a spinal rod to the bone anchor.

The above steps can be repeated to attach multiple extensions to the patient's spine. The multiple extensions can share common attachment points or can be attached at different locations. For example, first and second extensions can be placed in parallel on contralateral sides of the spinal midline. Inferior ends of the extensions can be attached to respective spinal rods and/or respective bone anchors of a primary construct. Superior ends of the extensions can be attached to respective attachment points longitudinally offset from the primary construct, or to a common attachment point such as a spinous process of a superior vertebra.

Figure 3:
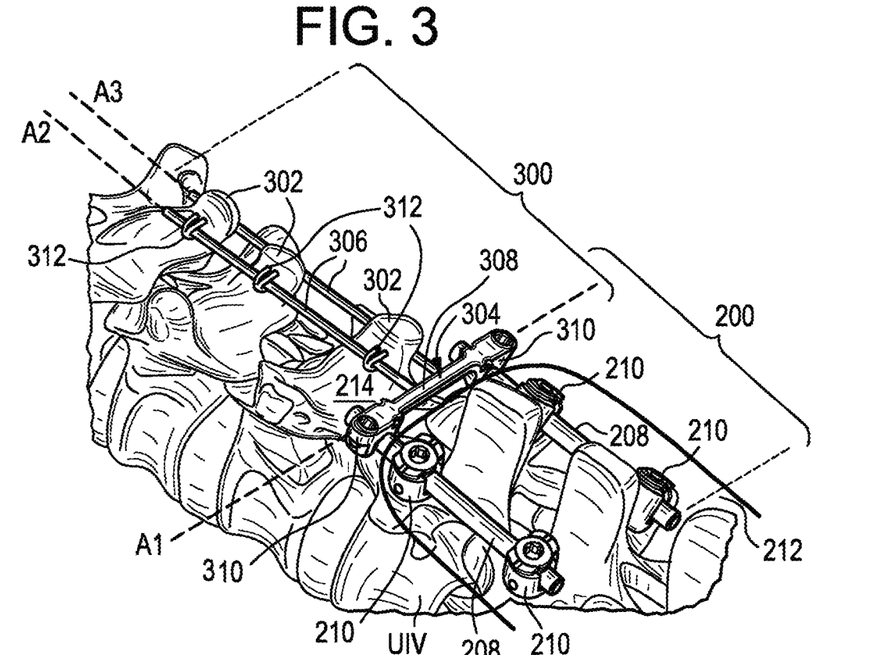
FIG. 3 is a perspective view of a connector attached to a patient's spine.

FIG. 3 illustrates an exemplary embodiment of an extension in the form of a connector 300 configured to be attached to a first attachment point (e.g., one or more spinous processes 302 of vertebrae superior to the primary construct 200) and to a second attachment point (e.g., one or more spinal rods 208 or bone anchors 210 of the primary construct).

As shown, the connector 300 can include a main body 304 with one or more arms 306 extending in a superior direction therefrom. The main body 304 can be or can include a transverse cross-connector of the type known in the art. Exemplary transverse cross-connectors are described in U.S. Pat. No. 7,717,938 entitled "DUAL ROD CROSS CONNECTORS AND INSERTER TOOLS"; U.S. Pat. No. 7,717,939 entitled "ROD ATTACHMENT FOR HEAD TO HEAD CROSS CONNECTOR"; and U.S. Pat. No. 8,361,117 entitled "SPINAL CROSS CONNECTORS" each of which is hereby incorporated by reference herein. The main body 304 can include any of the features of the cross-connectors described in the above patents. For example, the main body 304 can include one or more articulation joints to allow opposed rod connection points of the connector 300 to be movable relative to one another in one or more degrees of freedom. In the illustrated embodiment, the main body 304 includes a transverse strut 308 that extends between opposed free ends along an axis A1. Each end of the strut 308 can include a respective rod-receiving recess 310 and a set screw for locking a spinal rod within the rod-receiving recess. While rod-receiving recesses are shown, it will be appreciated that various other attachment features can be included instead or in addition. For example, one or both ends of the strut 308 can include an eyelet or other feature for attaching the strut directly to the head of a bone anchor 210.

The arms 306 can extend from the main body 304 in a superior direction. The arms 306 can extend along respective axes A2, A3. The arms 306 can be straight or can be curved, bent, or stepped in one or more planes. For example, the arms 306 can be curved in the sagittal plane to approximate a desired sagittal curvature of the patient's spine, or to exert extension forces on the patient's spine. The arms 306 can be rods, tubes, rails, and the like. The arms 306 can have a cross-section in a plane perpendicular to the arm axes A2, A3 that is cylindrical, oval, elliptical, square, or rectangular. The arms 306 be configured to frictionally and/or mechanically engage the first attachment point, e.g., the one or more spinous processes 302. For example, the surface of each arm 306 adjacent to the spinous processes 302 can include teeth, ridges, roughening, or other surface features or finishes for gripping and engaging the spinous processes. As another example, the arms 306 can have a geometry configured to wrap around a superior edge of the one or more spinous processes 302. The arms 306 can be bent or curved, or can include protrusions, shoulders, or other features that wrap around the superior edge of the spinous process 302. The arms 306 can be shaped such that, when implanted in a patient, a first portion of each arm contacts a lateral surface of a spinous process and a second portion of said arm contacts a superior surface of said spinous process.

The arms 306 can be less rigid than the spinal rod or rods 208 of the primary construct 200. For example, the arms 306 can have a smaller diameter or cross-section than the rods 208, and/or can be formed from a different material than the rods that is more flexible. The arms 306 can be cut to length to extend to the desired vertebral level, or can be used with the off-the-shelf length. The illustrated arms 306 extend from the main body 304 to three vertebral levels superior to the UIV of the primary construct 200. In other examples, the arms 306 can extend to one superior vertebral level, to two superior vertebral levels, or to more than three superior vertebral levels.

In use, the primary construct 200 can be implanted through a primary incision 212. The connector 300 can be inserted through the primary incision 212 and the arms 306 can be tunneled beneath the patient's skin and/or soft tissue 214 in a superior direction from the primary incision to the first attachment point. The arms 306 can be positioned on contralateral sides of the spinal midline. The arms 306 can be positioned such that they extend parallel to the rods 208 of the primary construct 200 in the coronal plane. The main body 304 of the connector 300 can be positioned such that it extends perpendicular to the rods 208 of the primary construct 200 in the coronal plane and/or perpendicular to the spinal midline in the coronal plane. The arms 306 can be positioned adjacent to or in contact with opposed lateral sides of the spinous processes 302 of one or more vertebrae superior to the UIV of the primary construct 200.

The arms 306 can be attached to the one or more spinous processes 302 by suturing 312 as shown, or with a screw, rivet, hook, clamp, or other attachment mechanism. The suture 312 or other attachment mechanism can extend transverse to the arms 306. The suture 312 or other attachment mechanism can be inserted through the primary incision 212, tunneled superiorly beneath the patient's skin and/or soft tissue 214, and affixed to the arms 306 and the spinous processes 302. A curved needle, a needle grasped with forceps, or other insertion instruments can be used to tunnel the suture 312 or other attachment mechanism. A superior terminal end of the primary incision 212 can be inferior to the first attachment point and/or inferior to the UIV of the primary construct 200, and the suture 312 or other attachment mechanism can be applied without extending the primary incision in the superior direction. Alternatively, or in addition, the suture 312 or other attachment mechanism can be applied via one or more secondary incisions disposed superior to the primary incision 212. The secondary incisions can be percutaneous or minimally-invasive incisions. The connector 300 can be installed as one piece or as separate components assembled in situ. For example, the arms 306 can be attached to the main body 304 while said components are disposed within the patient. A portion or the entirety of the connector 300 can be disposed superior to a superior terminal end of the primary incision 212 through which the primary construct 200 is implanted.

Figure 4:
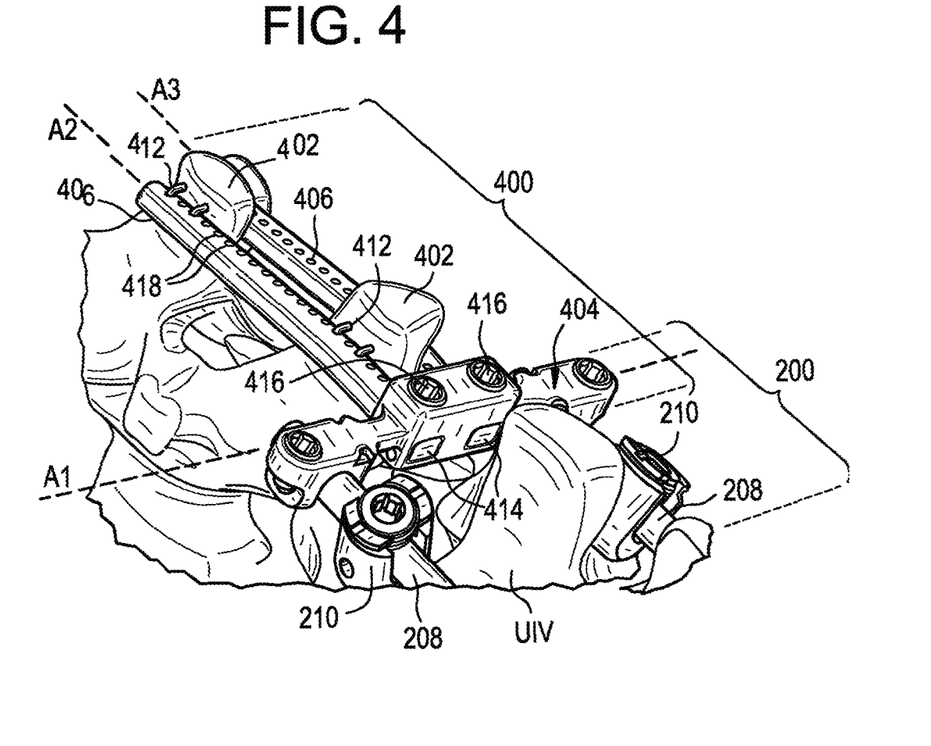
FIG. 4 is a perspective view of another connector attached to a patient's spine.

FIG. 4 illustrates an exemplary embodiment of an extension in the form of a connector 400 configured to be attached to a first attachment point (e.g., one or more spinous processes 402 of vertebrae superior to the primary construct 200) and to a second attachment point (e.g., one or more spinal rods 208 or bone anchors 210 of the primary construct). Except as indicated below and as will be readily appreciated by one having ordinary skill in the art in view of the present disclosure, the structure and operation of the connector 400 is the same as that of the connector 300 described above.

The connector 400 can include adjustable arms 406 that are movable relative to the main body 404 with one or more degrees of freedom. For example, the arms 406 can be slidably disposed in openings 414 formed in the main body 404 such that the arms can translate relative to the main body along the axes A2, A3. The openings 414 can be oversized relative to the exterior dimensions of the arms 406 to allow the arms to splay towards or away from each other, e.g., to accommodate wider or narrower spinous processes 402 therebetween, or to tilt in the sagittal plane, e.g., to adjust the attachment point along the height of the spinous processes 402. The connector 400 can include one or more locking elements 416 for selectively locking the position and/or orientation of the arms 406 with respect to the main body 404. For example, the main body 404 can include threaded recesses that intersect the openings 414 in which the arms 406 are slidably disposed. Set screws 416 can be threaded into the recesses and tightened to clamp the arms 406 within the main body 404 and prevent movement between the arms and the main body. While independent set screws 416 are shown, in some arrangements a single set screw can be used to simultaneously clamp both arms 406. Other locking mechanisms can be used instead or in addition to set screws, such as cam locks, threaded nuts, and the like. The arms 406 can include one or more apertures 418. The arms 406 can include a plurality of apertures 418 spaced along the length of the arms. The apertures 418 can be sized to receive a suture, rivet, screw, or other fastener 412 therethrough. The apertures 418 can be oriented perpendicular to the axes A1, A2, and A3 as shown.

Figure 5:
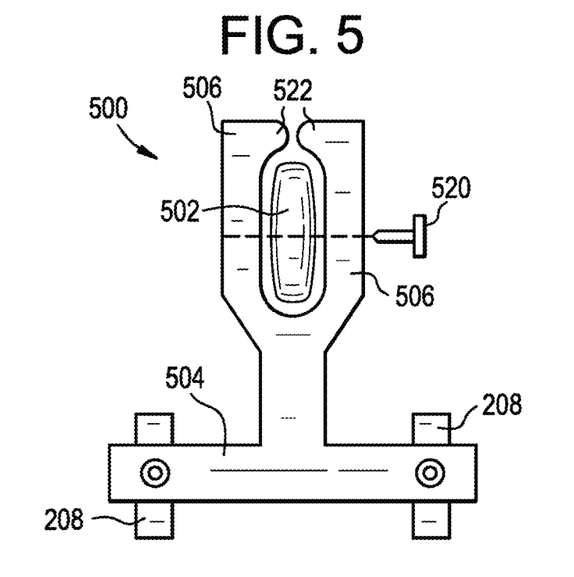
FIG. 5 is a top view of another connector attached to a patient's spine.

FIG. 5 illustrates an exemplary embodiment of an extension in the form of a connector 500 configured to be attached to a first attachment point (e.g., one or more spinous processes 502 of vertebrae superior to the primary construct 200) and to a second attachment point (e.g., one or more spinal rods 208 or bone anchors 210 of the primary construct). Except as indicated below and as will be readily appreciated by one having ordinary skill in the art in view of the present disclosure, the structure and operation of the connector 500 is the same as that of the connectors 300, 400 described above.

The arms 506 of the connector 500 can merge into a single arm as they approach the main body 504, forming a Y-shaped extension as shown. The arms 506 can be positioned on opposite lateral sides of a spinous process 502 and a screw, rivet, or other fastener 520 can be inserted therethrough to attach the arms to the spinous process. The arms 506 can be flexible. The arms 506 can be configured to move away from one another as the connector 500 is advanced in a superior direction over the spinous process 502 to allow the spinous process to enter a space defined between the arms. The arms 506 can be configured to then move towards one another to capture the spinous process 502 therebetween. The arms 506 can be configured to move further towards one another as the screw, rivet, or other fastener 520 is applied to the connector 500. The arms 506 can attach to a single spinous process 502 as shown or to multiple spinous processes.

The arms 506 can have a geometry configured to wrap around a superior edge of the one or more spinous processes 502. The arms 506 can be bent or curved, or can include protrusions, shoulders, or other features 522 that wrap around the superior edge of the spinous processes 502. The arms 506 can be shaped such that, when implanted in a patient, a first portion of each arm contacts a lateral surface of a spinous process and a second portion of said arm contacts a superior surface of said spinous process.

Figure 6:
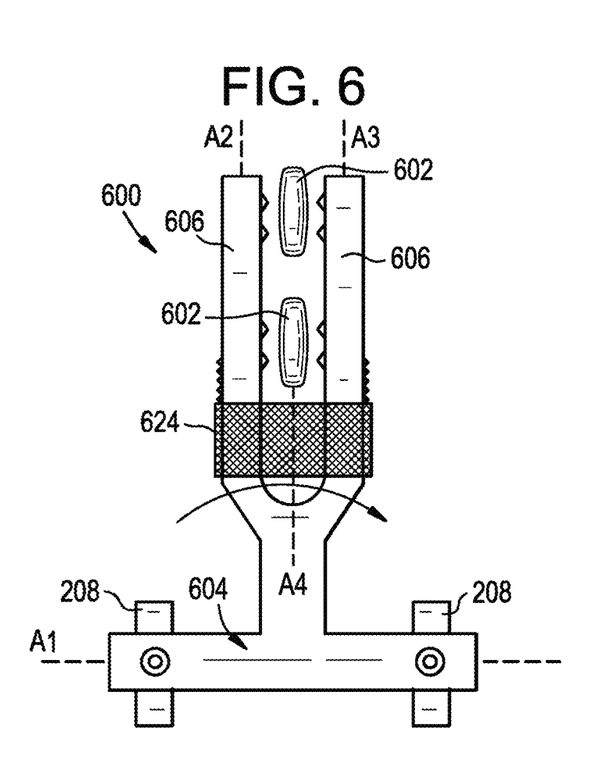
FIG. 6 is a top view of another connector attached to a patient's spine.

FIG. 6 illustrates an exemplary embodiment of an extension in the form of a connector 600 configured to be attached to a first attachment point (e.g., one or more spinous processes 602 of vertebrae superior to the primary construct 200) and to a second attachment point (e.g., one or more spinal rods 208 or bone anchors 210 of the primary construct). Except as indicated below and as will be readily appreciated by one having ordinary skill in the art in view of the present disclosure, the structure and operation of the connector 600 is the same as that of the connectors 300, 400, 500 described above.

The connector 600 can include a rotatable or slidable ring or collar 624 through which the arms 606 extend. The collar 624 can be rotatable relative to the arms 606 about an axis A4 that is perpendicular to the axis A1 in the coronal plane and parallel or substantially parallel to the axes A2, A3 in the coronal plane. A central opening of the collar 624 can include an interior thread that interfaces with an exterior thread formed on the arms 606. The threads of the collar 624 and/or the threads of the arms 606 can be tapered such that rotating the collar in a first direction squeezes the arms towards one another, e.g., to clamp onto a spinous process 602 disposed between the arms, and rotation of the collar in a second, opposite direction allows the arms to move away from each other, e.g., to release from a spinous process disposed between the arms. Interior surfaces of the arms 606 can include teeth, spikes, or other surface features or treatments for biting into the spinous processes 602 and enhancing the grip on the spinous processes. The arms 606 can be resilient or can be otherwise biased towards the released position. In other arrangements, the collar 624 can be slidably disposed over the arms 606 and can be configured to translate relative thereto along the axis A4, with or without rotating the collar relative to the arms. The collar 624 and/or the arms 606 can be tapered such that sliding the collar in the superior direction relative to the arms causes the arms to move towards each other and sliding the collar in the inferior direction relative to the arms allows the arms to move away from each other. The arms 606 can attach to multiple spinous processes 602 as shown or to a single spinous process.

In use, the connector 600 can be inserted through the primary incision used to implant the primary construct 200. The opposed arms 606 can be tunneled in a superior direction and positioned on opposite lateral sides of one or more spinous processes 602 of vertebrae superior to the UIV of the primary construct 200. The collar 624 can then be rotated or slid relative to the arms 606 to move the arms towards one another and clamp the arms onto the one or more spinous processes. The main body 604 of the connector can be attached to the primary construct 200, e.g., by clamping onto one or more rods 208 of the primary construct.

Figure 7:
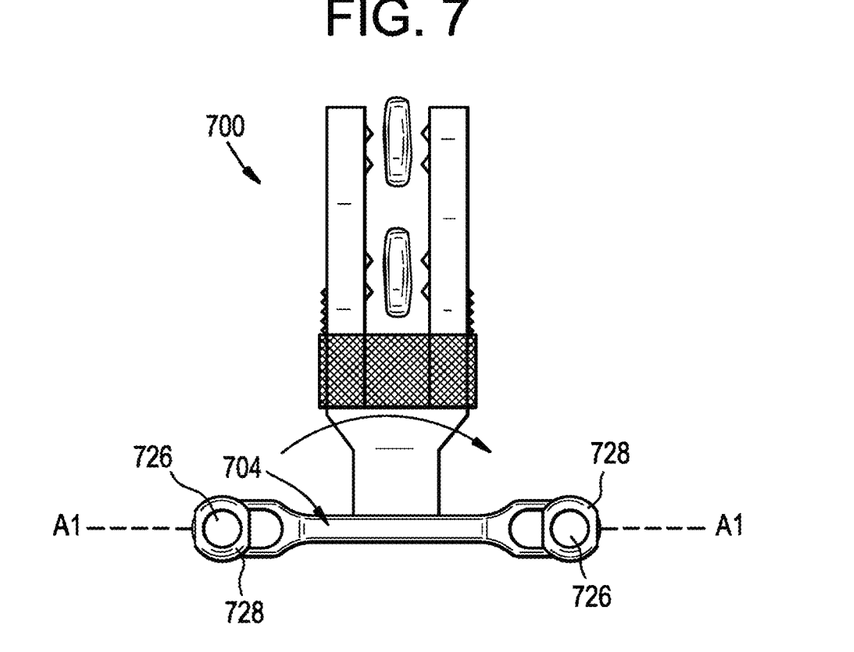
FIG. 7 is a top view of another connector attached to a patient's spine.

While the connectors 300, 400, 500, 600 above are shown with a main body having a rod-to-rod connection, it will be appreciated that other arrangements can be used instead or in addition. For example, any of the connectors described herein can include a main body configured for attachment directly to first and second bone anchors, such as pedicle or lateral mass screws, of the primary construct. FIG. 7 illustrates an exemplary connector 700 that is similar to the connector 600 described above, but includes a main body 704 with opposed eyelets 726. The eyelets 726 can be configured to attach to respective bone anchors. For example, each eyelet 726 can receive a threaded post that extends proximally from a bone anchor, and a nut can be advanced over the threaded post to secure the main body 704 to the bone anchor. The eyelets 726 can be formed in washers 728, which can be movably coupled to the main body 704. For example, the washers 728 can be slidable along the axis A1 relative to the main body 704.

Figure 8:
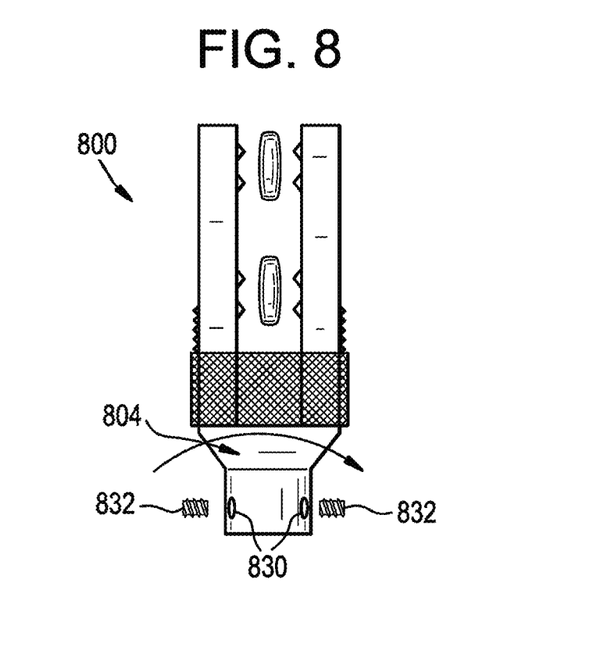
FIG. 8 is a top view of another connector attached to a patient's spine.

The connectors 300, 400, 500, 600 above can be rigidly attached to the primary construct 200, or can be flexibly attached thereto. For example, any of the connectors described herein can include a main body with apertures or other features for attaching the main body to the primary construct using one or more flexible tethers or other linkages. FIG. 8 illustrates an exemplary connector 800 that is similar to the connector 600 described above, but includes a main body 804 with opposed apertures 830 for receiving one or more flexible tethers, which can in turn be clamped or otherwise attached to the primary construct 200. The connector 800 can include screws or other locking elements 832 for clamping onto a tether extending through the apertures 830. In one arrangement, a single tether can be attached to a first spinal rod of the primary construct 200, extend superiorly to the connector 800, pass through both apertures 830 of the connector, and return inferiorly to attach to a second contralateral spinal rod of the primary construct. In another arrangement, a first tether can be attached to a first spinal rod of the primary construct 200, extend superiorly to the connector 800, and attach to a first aperture 830 of the connector. A second tether can be attached to a second contralateral spinal rod of the primary construct 200, extend superiorly to the connector 800, and attach to a second aperture 830 of the connector.

The connectors disclosed herein can be implanted by inserting the connector through a primary incision through which the primary construct is implanted, and then tunneling the arms of the connector through tunnels formed alongside or towards the first attachment point(s), e.g., one or more spinous processes of superior vertebrae. The tunnels can be formed beneath the skin and/or soft tissue of the patient. The tunnels can be formed in a muscle-sparing fashion. A fastener used to attach the arms to the first attachment point(s) can be applied through the same tunnels or through a separate tunnel. An instrument for applying the fastener can be inserted through the same tunnels or through a separate tunnel. These techniques can be used to reduce the number of incisions and the amount of tissue disruption associated with placing the construct and the connector, which can help prevent PJK/PJF.

In an exemplary arrangement, an insertion jig can be attached to the connector and can be rotated about the attachment point to guide a rivet, suture, needle, screw, or other fastener through an arc that intersects a predetermined target location along the arms of the connector. The insertion jig can thereby consistently and accurately guide the fastener to the desired location, even when the desired location is not visible because it is beneath the skin and/or soft tissue of the patient. The insertion jig can be detached from the connector and removed prior to closing the patient.

In another exemplary arrangement, the connector can define a groove, track, or ridge for guiding a rivet, suture, needle, screw, or other fastener to a predetermined target location along the arms of the connector. An inserter instrument, such as a riveting tool, can be guided along the groove, track, or ridge to align the operating end of the instrument with the desired location for applying the fastener. The arms of the connector can have an I-beam cross-section, or can otherwise include a guide track through which an instrument can be guided to apply a fastener in the desired location.

Figure 9:
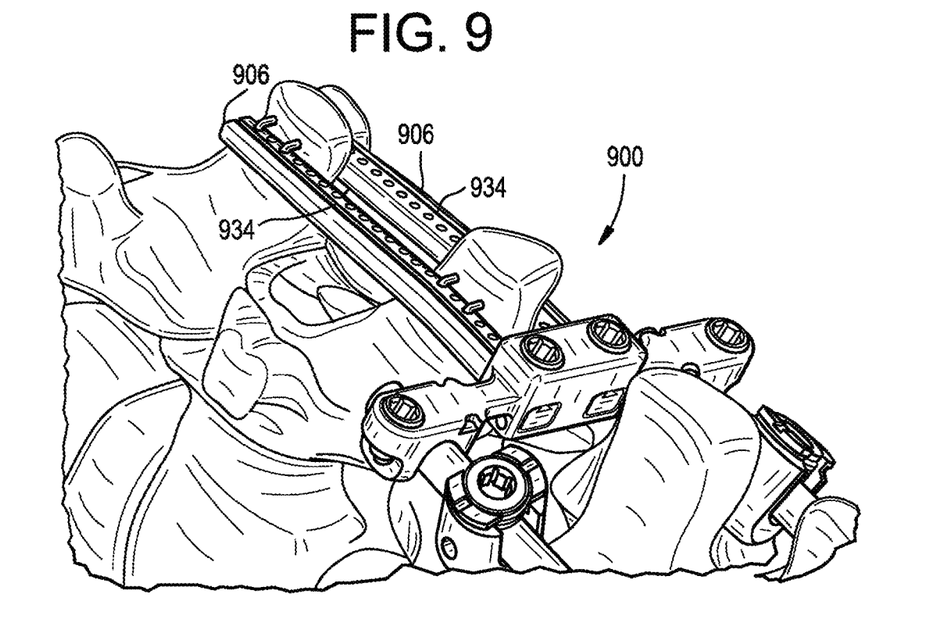
FIG. 9 is a perspective view of another connector attached to a patient's spine.

FIG. 9 illustrates an exemplary connector 900 having guide tracks formed in or on the arms 906 of the connector. As shown, one or both arms 906 can include a guide track 934 formed in or on a posterior face of the arm. The guide track 934 can extend in a caudal-to-cranial direction. The guide track 934 can be a groove, recess, track, ridge, and/or protrusion formed on the arm 906. The guide track 934 can have a rectangular transverse cross section. The guide track 934 can be formed in the center or substantially in the center of the posterior surface of the arm 906. While the illustrated connector 900 is similar to the connector 400 described above, it will be appreciated that any of the connectors herein can include similar guide tracks.

Figure 10:
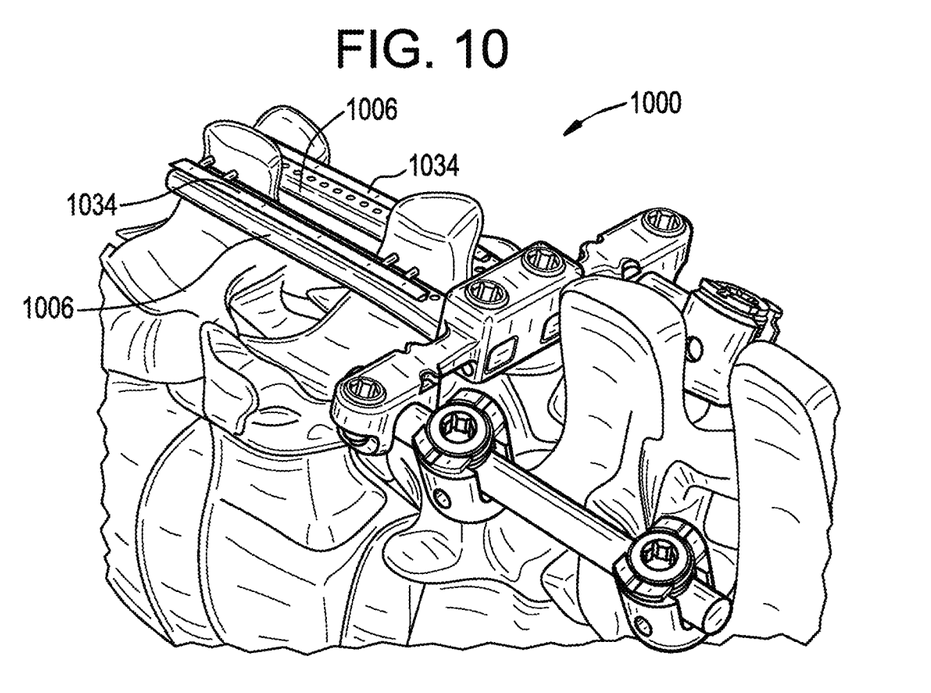
FIG. 10 is a perspective view of another connector attached to a patient's spine.

FIG. 10 illustrates an exemplary connector 1000 having guide tracks formed in or on the arms 1006 of the connector. As shown, one or both arms 1006 can include a guide track 1034 formed in or on a posterior face of the arm. The guide track 1034 can extend in a caudal-to-cranial direction. The guide track 1034 can be a groove, recess, track, ridge, and/or protrusion formed on the arm 1006. The guide track 1034 can have a dovetail transverse cross section. For example, the guide track 1034 can be a protrusion that extends posteriorly from a posterior surface of the arm 1006, the protrusion having opposed lateral sidewalls that taper obliquely towards one another in a posterior-to-anterior direction. Instruments guided by the guide track 1034 can include a counterpart dovetail groove for mating with the guide track, which can facilitate retention of the instrument to the guide track. The guide track 1034 can be formed in the center or substantially in the center of the posterior surface of the arm 1006. While a male dovetail feature is shown, the arms 1006 can instead include a female dovetail feature configured to receive a male dovetail feature of an instrument. While the illustrated connector 1000 is similar to the connector 400 described above, it will be appreciated that any of the connectors herein can include similar guide tracks.

Figure 11:
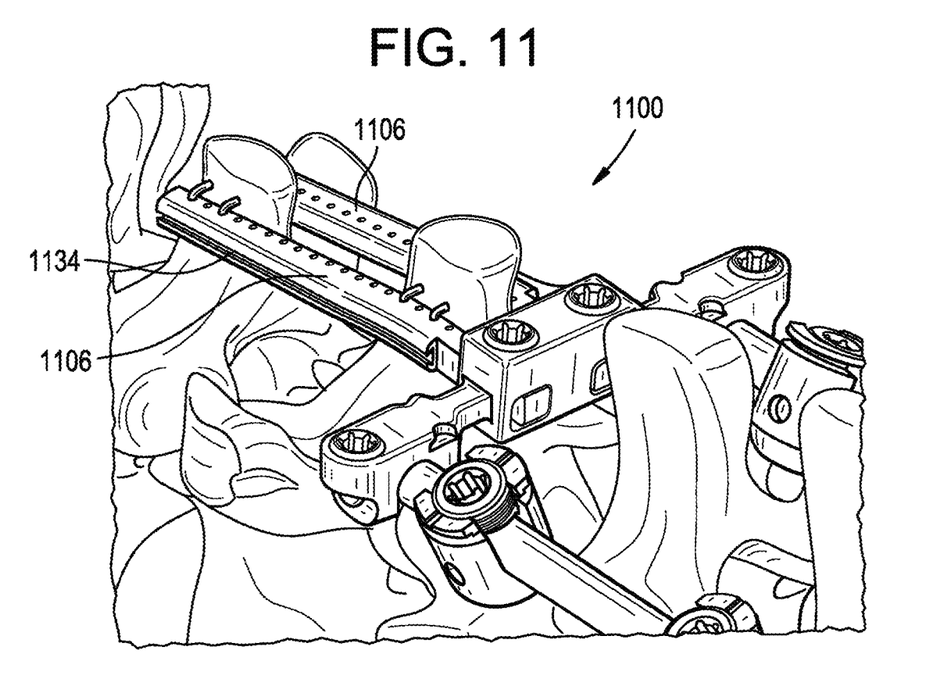
FIG. 11 is a perspective view of another connector attached to a patient's spine.

FIG. 11 illustrates an exemplary connector 1100 having guide tracks formed in or on the arms 1106 of the connector. As shown, one or both arms 1106 can include a guide track 1134 formed in or on a lateral face of the arm. The guide track 1134 can extend in a caudal-to-cranial direction. The guide track 1134 can be a groove, recess, track, ridge, and/or protrusion formed on the arm 1106. The guide track 1134 can have a dovetail transverse cross section. For example, the guide track 1134 can be a recess that extends inward from a lateral surface of the arm 1106, the recess having opposed anterior and posterior sidewalls that taper obliquely towards one another in a medial-to-lateral direction. Instruments guided by the guide track 1134 can include a counterpart dovetail protrusion for mating with the guide track, which can facilitate retention of the instrument to the guide track. The guide track 1134 can be formed in the center or substantially in the center of the lateral surface of the arm 1106. While a female dovetail feature is shown, the arms 1106 can instead include a male dovetail feature configured to be receive in a female dovetail feature of an instrument. While the illustrated connector 1100 is similar to the connector 400 described above, it will be appreciated that any of the connectors herein can include similar guide tracks.

Figure 12:
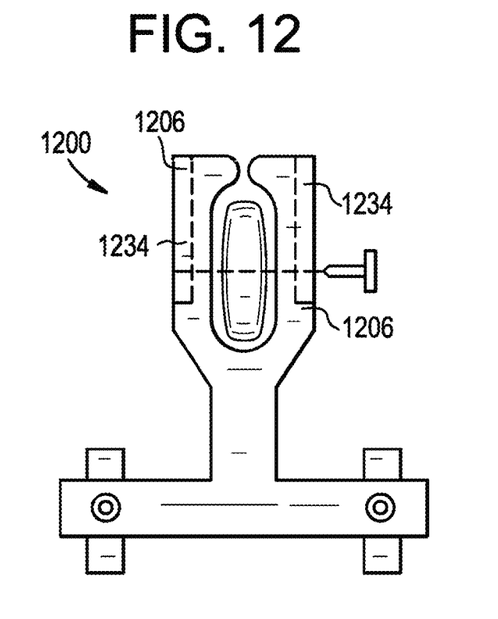
FIG. 12 is a top view of another connector attached to a patient's spine.

FIG. 12 illustrates an exemplary connector 1200 having guide tracks formed in or on the arms 1206 of the connector. As shown, one or both arms 1206 can include a guide track 1234 formed therein or thereon. The guide track 1234 can extend in a posterior-to-anterior direction. The guide track 1234 can be a groove, recess, track, ridge, and/or protrusion formed on the arm 1206. The guide track 1234 can have a dovetail transverse cross section. Instruments guided by the guide track 1234 can include a counterpart dovetail feature for mating with the guide track, which can facilitate retention of the instrument to the guide track. The guide track 1234 can be formed in the center or substantially in the center of the arm 1206. While the illustrated connector 1200 is similar to the connector 500 described above, it will be appreciated that any of the connectors herein can include similar guide tracks.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

While extension of a construct in a superior direction is generally described above, it will be appreciated that the systems and methods disclosed herein can also be used to extend a construct in an inferior direction, or solely within the superior and inferior limits of a primary construct, e.g., to reinforce the primary construct.

While the systems and methods disclosed herein are generally described in the context of spinal surgery with rigid spinal fixation constructs, it will be appreciated that the systems and methods herein can be used with various other types of fixation or stabilization hardware, in any bone, in non-bone tissue, or in non-living or non-tissue objects. The systems disclosed herein and the various component parts thereof can be fully implanted, or can be used as part of an external fixation or stabilization system. The systems and methods disclosed herein can be used in minimally-invasive surgery and/or open surgery.

The systems disclosed herein and the various component parts thereof can be constructed from any of a variety of known materials. Exemplary materials include those which are suitable for use in surgical applications, including metals such as stainless steel, titanium, cobalt-chromium, titanium-molybdenum, or alloys thereof, polymers such as PEEK, ceramics, carbon fiber, and so forth. The various components of the systems disclosed herein can be rigid or flexible. One or more components or portions of the system can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

Although specific embodiments are described above, it should be understood that numerous changes may be made within the spirit and scope of the concepts described.

The invention claimed is:

1. A surgical system, comprising:
a primary construct comprising a rigid spinal fixation rod and first and second bone anchors configured to attach the spinal rod to first and second vertebrae; and
a connector comprising:
a unitary main body that runs along a first axis and having at least one attachment point for attaching the connector to the primary construct; and
first and second arms coupled to the main body, the first and second arms having guide tracks formed therein or thereon that extend from terminal ends thereof toward the main body and face in opposite directions on opposed surfaces of the first and second arms, the first and second arms having one or more apertures formed on a surface of each arm that is perpendicular to the opposed surfaces, the first and second arms extending perpendicular to the first axis.

2. The system of claim 1, further comprising a second rigid spinal fixation rod, wherein the at least one attachment point comprises first and second rod receiving recesses disposed at opposite ends of the main body, and wherein the main body includes a transverse strut extending between the first and second rod receiving recesses, and wherein the first and second arms are coupled to the transverse strut.

3. The system of claim 1, wherein the arms include bone engaging teeth or surface features formed thereon.

4. The system of claim 1, wherein the arms are shaped to wrap around the superior edge of a spinous process.

5. The system of claim 1, wherein the arms are shaped to simultaneously contact a lateral surface of a spinous process and a superior surface of said spinous process.

6. The system of claim 1, wherein the arms are more flexible than the spinal rod.

7. The system of claim 1, wherein the arms extend from the main body by a length of at least two vertebral levels of an adult human patient.

8. The system of claim 1, wherein the arms merge into a single arm as they approach the main body.

9. The system of claim 1, further comprising an elongate flexible tether insertable through one or more openings formed in the main body of the connector.

10. The system of claim 9, wherein the main body is coupled to one or more locking elements configured to clamp onto the tether when the tether is disposed through the one or more openings.

11. The system of claim 1, wherein the guide track has a dovetail transverse cross section.

* * * * *